United States Patent
Schuerch

(10) Patent No.: US 7,731,141 B2
(45) Date of Patent: Jun. 8, 2010

(54) SURGICAL APPLIANCE POST CLAMP FOR SURGICAL TABLES

(76) Inventor: Peter Schuerch, 42 Bayview Ave., Quincy, MA (US) 02043

( * ) Notice: Subject to any disclaimer, the term of this patent is extended or adjusted under 35 U.S.C. 154(b) by 579 days.

(21) Appl. No.: 11/398,934

(22) Filed: Apr. 6, 2006

(65) Prior Publication Data

US 2006/0229500 A1   Oct. 12, 2006

Related U.S. Application Data

(60) Provisional application No. 60/668,551, filed on Apr. 6, 2005.

(51) Int. Cl.
*A47B 96/06* (2006.01)
*A47G 1/00* (2006.01)
*A61G 13/00* (2006.01)

(52) U.S. Cl. .............................. 248/230.3; 248/229.12; 248/316.4; 248/218.4; 5/624; 5/648; 269/81; 403/373

(58) Field of Classification Search ............ 248/231.51, 248/286.1, 230.3, 316.6, 230.1, 231.41, 218.4, 248/229.11, 229.26, 316.4, 229.12; 5/621, 5/658, 600, 618, 624, 630, 648; 403/59, 403/389, 260, 257, 373, 256; 269/48.2, 74, 269/81
See application file for complete search history.

(56) References Cited

U.S. PATENT DOCUMENTS

| 2,933,567 | A | * | 4/1960 | Mageoch | 191/40 |
| 4,085,818 | A | * | 4/1978 | Swager | 182/48 |
| 4,547,092 | A | * | 10/1985 | Vetter et al. | 403/59 |
| 4,796,846 | A | * | 1/1989 | Meier et al. | 248/286.1 |
| 5,135,210 | A | * | 8/1992 | Michelson | 5/658 |
| 5,538,215 | A | * | 7/1996 | Hosey | 248/286.1 |
| 5,836,559 | A | * | 11/1998 | Ronci | 248/230.3 |
| 6,622,980 | B2 | * | 9/2003 | Boucher et al. | 248/231.51 |
| 7,003,827 | B2 | * | 2/2006 | DeMayo | 248/229.14 |
| 7,020,917 | B1 | * | 4/2006 | Kolody et al. | 5/621 |
| 7,159,832 | B2 | * | 1/2007 | Easterling | 248/316.6 |

* cited by examiner

*Primary Examiner*—Amy J Sterling
*Assistant Examiner*—Tan Le
(74) *Attorney, Agent, or Firm*—John M. Brandt

(57) ABSTRACT

A clamp for securing a surgical appliance post to a rail mounted on the side of a surgical table which clamp may be placed over and on the rail at any desired location by providing the clamp body with a passageway transverse the body of the clamp and parallel to the rail, the passageway having a lip on one edge of a width about the dimension of the rail for engaging the backside of the rail, and the passageway having a width greater than the rail on the opposite edge. A clamping device such as a screw or cam is mounted on the outermost portion of the clamp and is arranged to engage and secure the post as well as bind the clamp body to the rail. Additionally, the clamping arrangement of one of the preferred embodiments provides a means by which an appliance post may be gripped at any chosen angle rather than limited to a fixed orientation.

2 Claims, 4 Drawing Sheets

SURGICAL APPLIANCE POST CLAMP FOR SURGICAL TABLES

CROSS-REFERENCE TO RELATED APPLICATIONS

This application is based on the disclosure of Provisional Application Ser. No. 60/668,551 filed Apr. 6, 2005 by the same inventor which is hereby incorporated by reference.

BACKGROUND OF THE INVENTION

1. Field of the Invention

The invention resides in the field of clamping devices for apparatus used in conjunction with surgical tables for medical operations.

2. Description of the Prior Art

Surgical tables for medical operations are almost universally equipped with a rail disposed about their edges to which may be affixed a post holding clamp. The rails are spaced apart from the table edge a standard distance and are of uniform dimension. The prior art clamps used with these rails have a channel oriented to the longitudinal axis of the rail which channel is slightly larger than the rail to allow the clamp to be slid along and positioned on the rail at a desired location. Gaps are provided in the rail to allow the clamp to be put on and taken off the rail as the need arises. The present invention eliminates the need for such gaps by providing, in the clamp body, a rail engaging passageway of different dimensions on each edge allowing the clamp to be placed on the rail at any desired location.

SUMMARY OF THE INVENTION

The invention may be summarized as an operating table clamp attachable to a side rail mounted on such tables for the purpose of securing surgical appliances in position during a surgical procedure. Such appliances are, among other devices, immobilizing supports or rests for body components and must be held in a secure and rigid manner. Posts of a standardize size and configuration are attached to the appliances to provide the means for mounting to the rail. Previously, clamps for joining the posts and rail had a passageway in the clamp body for receiving the rail which required gaps in the rail in order to slide the clamp on the rail. Alternatively, clamp bodies hinged on one side to open the passageway have been employed with means to swing and lock the hinged portion in place.

The invention herein utilizes a clamp body with a rail receiving passageway having one edge the size of the rail and the opposite edge larger than the rail to allow that passageway edge of the clamp body to be placed over the rail and then swung into place against the rail. The entire clamp, the post and the rail are then locked together by a clamping device such as a bolt or cam.

Two separate embodiments are described below. The first has such a passageway transverse the clamp body. A post port perpendicular to the passageway is provided for receiving an apparatus post and a clamping member is used to bind the post, clamp, and rail. A second perpendicular rail port adjacent the post port will engage a rail in the same manner as an alternative to the post.

In the second embodiment, additional clamping members are added to form a clamping assembly which allows the appliance post to be positioned and gripped at any angle with respect to the table and rail. These consist for example in addition to a bolt as above, a rotatable drum, and a clamp body extension, each with a co-alignable port for receiving the post, and a rail engaging extension. The various parts or clamping members fit together in a unique way to form the total clamping assembly to accomplish the purpose of the invention.

These and other features and advantages of the invention will be more fully understood from the description of the preferred embodiments taken with the drawings which follows.

DESCRIPTION OF THE PREFERRED EMBODIMENT

Figure 1:
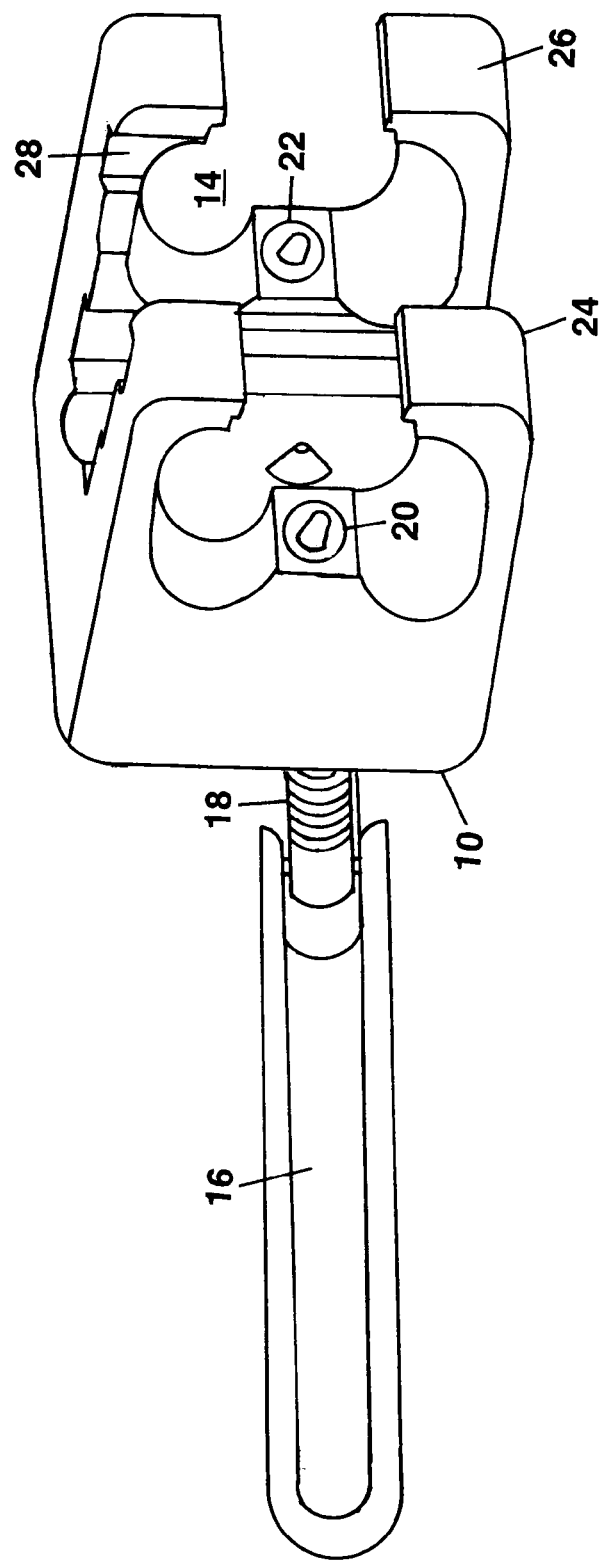
FIG. 1 is a perspective view of a first preferred embodiment of the invention.

Referring first to FIG. 1, there is shown a perspective illustration of a first preferred embodiment of the invention consisting of a clamp body 10 having surgical table rail receiving passage 12, post receiving port 14, clamping handle 16 operating clamping bolt 18, and rail spring biasing members 20 and 22 Post receiving port. 14 divides the first portion of body 12 into two spaced apart rail gripping extensions 24 and 26. Adjacent to and communicating with port 14 is a second port 28 sized to receive a length of surgical table rail.

Figure 2:
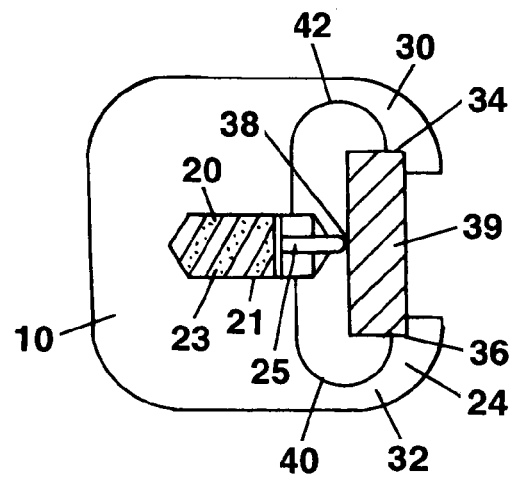
FIG. 2 is a cross-sectional side view of the embodiment of FIG. 1.

FIG. 2 is a cross-sectional side view of the clamp of FIG. 1 through rail gripping extension 24 and rail spring biasing member 20. As shown, both upper 30 and lower 32 front portions of extension 24 have lips 34 and 36 respectively, which, in conjunction with the tip 38 of spring biasing member 20, form an edge the size of rail 39. The edges 40 and 42 opposite the lip edges are larger than the width of the rail.

Figure 3:
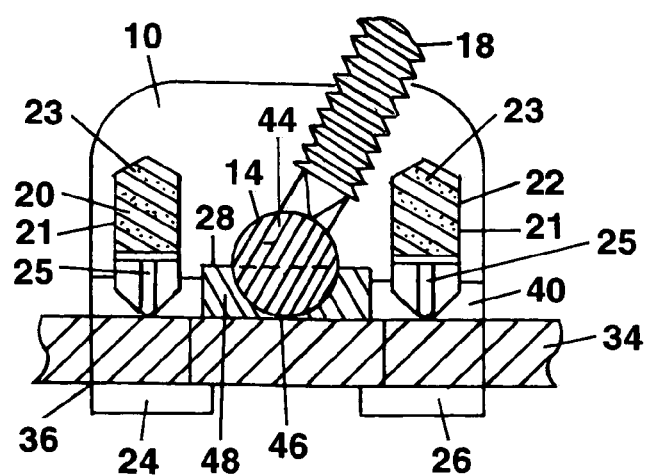
FIG. 3 is a cross-sectional top view of the embodiment of FIG. 1.

As further shown in FIG. 2, spring biasing member 20 consists of a well 21 disposed in clamp body 10, a spring 23 disposed in well 21, and a spring follower or plunger 25 terminating in tip 38 also disposed in well 21 forward of spring 23. As shown in FIG. 3, spring biasing member 22 is of the same construction as that of member 20.

FIG. 3 is a cross-sectional top view of FIG. 1 illustrating the manner in which clamp 10, rail 38, and post 44 are bound together by the force of bolt 18 as it is turned toward rail 39 by handle 16. Clamp body 10 is drawn outward from rail 39 while post 44 is forced against the rail at contact point 46. Alternatively, a rail 48 of the same dimension as the table rail for attaching surgical appliances may be vertically disposed in port 28, it being understood that either post 44 or rail 48 may be employed during a surgical procedure but not both at the same time.

Figure 4:
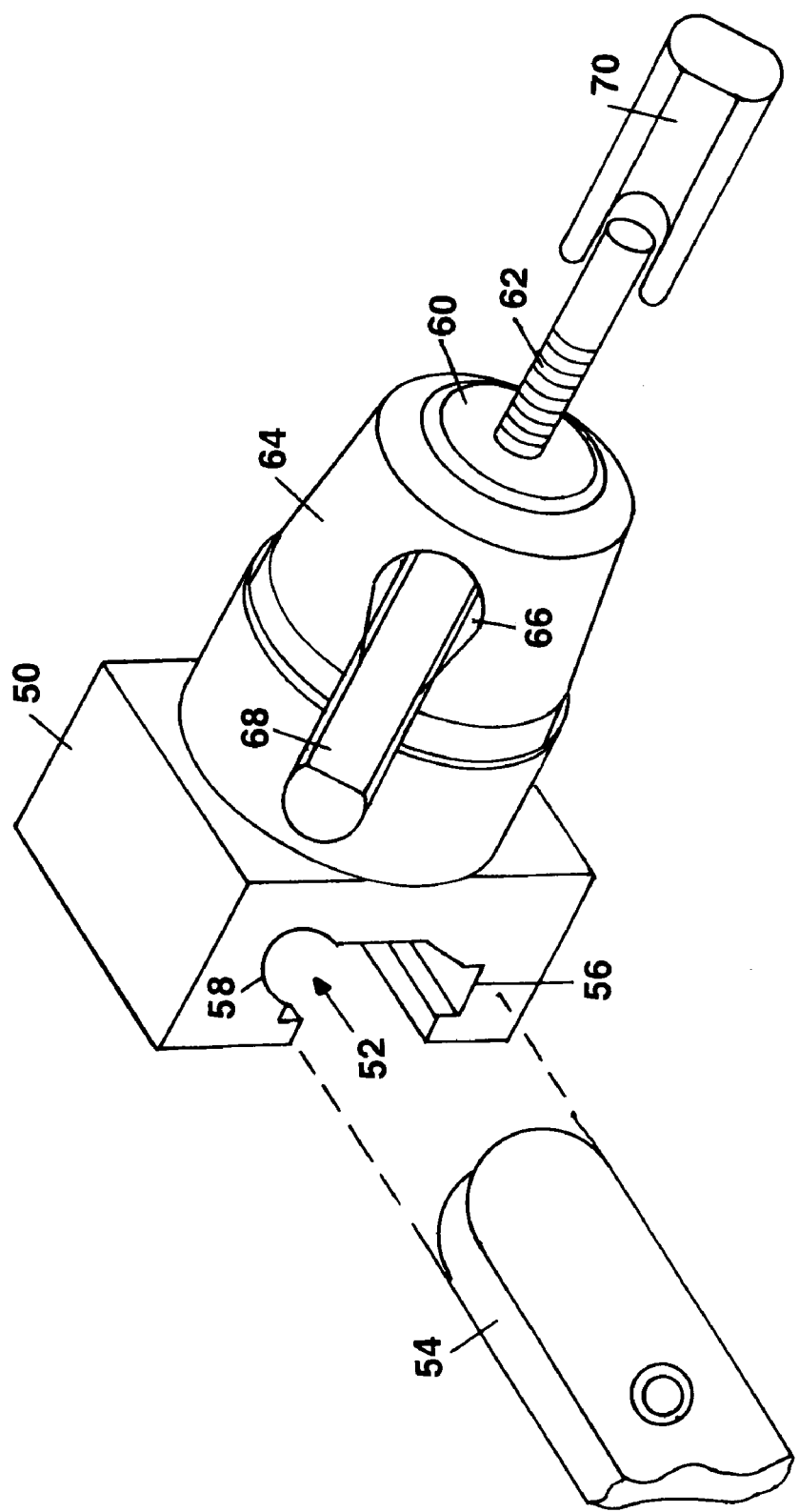
FIG. 4 is a perspective view of another preferred embodiment of the invention.

Referring next to FIG. 4, a perspective view of a second preferred embodiment of the invention is shown which provides for positioning the post at any desired angle with relation to the table rail. Clamp body 50 has passageway 52 extending completely across the length of the body for receiving surgical table rail 54. Passageway 52 is about the width of the rail along side 56 and greater than the rail along side _58. Clamping members 60, 62, and 64 form a clamping assembly which will be further illustrated and described below. The assembly has port 66 consisting of co-aligning ports in members 64 and 60 for receiving a surgical appliance post 68. Handle 70, when rotated, will draw clamp members 62 and 64 together securing post 68 between clamp members 62 and 64, and forcing clamp member 64 against rail 54 to bind the entire combination of rail post and clamp.

Figure 5:
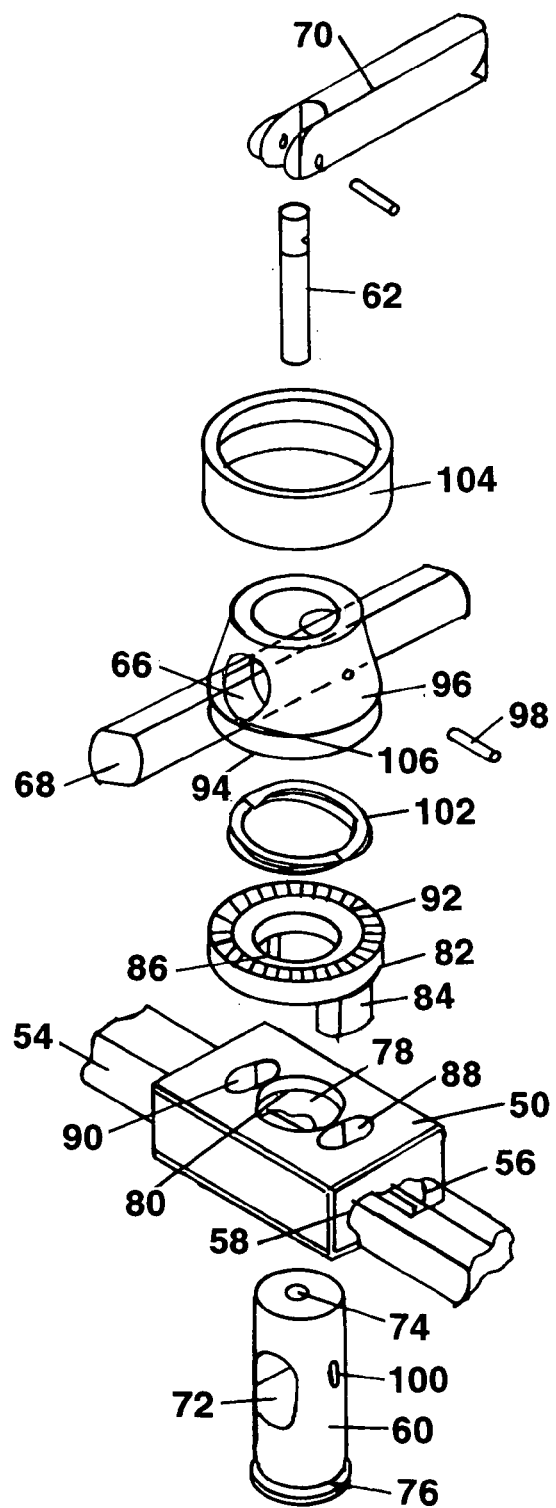
FIG. 5 is a broken out perspective view of the embodiment of FIG. 4.

FIG. 5 illustrates the components of the clamp of FIG. 4 broken out to show the interaction of the constituent parts. Clamp member 60 consists of a cylinder having post receiving port 72 and a threaded hole 74 for receiving clamp member 62, a bolt for example. The bottom of the cylinder is expanded into a lip 76. Clamp member 60 fits inside clamp body 50 extending upwards through port 78 and is limited in travel by lip 76 secured against the under topside 80 of clamp body 50.

Clamp member 64 consists of two parts. The first is a ring 82 having downward extending rail engaging members 84 and 86 which fit through ports 88 and 90 in body 50 to contact and bind rail 54 when the entire clamp system is compressed. The top 92 of ring 82 is serrated to engage the opposing serrations 94 formed on the bottom of body portion 96 forming the second part of clamp member 64. Body portion 96 has post-receiving port 66 which aligns with port 72 in clamp member 60 and is secured in position by pin 98 fitting into slot 100. Slot 100 has sufficient height to allow clamp member 64 parts 82 and 96 to slightly separate to allow body portion 96 to rotate free of the engagement of the serrations as described above.

Compressible spring 102 fits between ring 82 and body portion 96 to provide lateral tension. Guide ring 104 fits over ring 82 and the lower part of body portion 96 to provide alignment and secure spring 102.

In operation, clamp member or bolt 62 is rotated by handle 70 into hole 74 in clamp member 60 drawing the two parts together. This forces lip 76 of clamp member 60 against the underside 80 of clamp body 50 and binds post 68 against the lower surface 106 of port 66 in clamp member 64. As will be seen, when ring 82 and body portion 96 are separated, body portion 96, clamp member 64 and post 68 are free to rotate to orient the post. When these components are drawn together by the rotation of bolt 62 into clamp member 60, the opposing serrations 92 and 94 mate to secure the post in place at the desired angle.

As variations in the above described embodiments will now be apparent to those skilled in the art, the invention is accordingly defined by the following claims.

What is claimed is:

1. A clamp for attaching a post equipped surgical appliance to a rail attached to a surgical operating table, said rail having a front face and a back face and a top longitudinal edge and a bottom longitudinal edge, comprising in combination:
   A. a clamp body for engaging said rail, said body having a passageway transverse said body for receiving said rail, one side of said passageway having a lip of a width substantially equal to the width of said rail and the opposite side of said passageway having a width sufficiently greater than said rail to allow said clamp body to be placed over and against said rail from either longitudinal edge of said rail;
   B. retractable spring biasing means disposed within said clamp body positioned on said opposite side of said passageway across from said lip, said spring biasing means arranged to engage said rail face nearest said clamp body opposite said lip to bias said clamp body away from said rail and said lip when said clamp body is placed over said rail whereby said clamp body and said rail are firmly engaged prior to clamping; and
   C. a post clamp assembly attached to said clamp body and arranged, upon activation, to bind said clamp body and said post to said rail at a selected location on said table wherein said clamp body further has:
      i. a first channel disposed in said clamp body connecting with and substantially perpendicular to said passageway for receiving said post; and
      ii. a second threaded channel disposed in said clamp body communicating with said first channel and wherein said clamp assembly comprises a threaded rod communicating with said second threaded channel whereby upon rotating said rod, said rod will engage said post and said post will engage said rail.

2. The clamp of claim 1 wherein said spring biasing means comprises:
   A. a well disposed in said clamp body opposite side;
   B. a spring disposed in said well; and
   C. a spring follower disposed in said well communicating with said spring and said rail.

\* \* \* \* \*